US007435732B2

(12) United States Patent
Tong et al.

(10) Patent No.: US 7,435,732 B2
(45) Date of Patent: Oct. 14, 2008

(54) CRYSTALLINE POLYMORPHS OF (3S)-N-HYDROXY-4-({4-[-(4-HYDROXY-2-BUTYNYL)OXY]PHENYL}SULFONYL)-2,2-DIMETHYL-3-THIOMORPHOLINE CARBOXAMIDE

(75) Inventors: Wei Tong, Suffern, NY (US); Abdolsamad Tadayon, Kirkland (CA); Peter John Larkin, Stratford, CT (US); Lalitha Krishnan, Suffern, NY (US); Subodh S. Deshmukh, White Plains, NY (US); Jean Marie Akin, Cross River, NY (US)

(73) Assignee: Wyeth, Madison, NJ (US)

( * ) Notice: Subject to any disclaimer, the term of this patent is extended or adjusted under 35 U.S.C. 154(b) by 459 days.

(21) Appl. No.: 11/146,730

(22) Filed: Jun. 7, 2005

(65) Prior Publication Data

US 2005/0272929 A1    Dec. 8, 2005

Related U.S. Application Data

(60) Provisional application No. 60/577,784, filed on Jun. 8, 2004.

(51) Int. Cl.
*C07D 279/12* (2006.01)
*A61K 31/54* (2006.01)

(52) U.S. Cl. .................... 514/227.5; 544/58.4
(58) Field of Classification Search ............... 544/58.4; 514/227.5
See application file for complete search history.

(56) References Cited

U.S. PATENT DOCUMENTS

| 6,153,757 A | 11/2000 | Zook et al. |
| 6,225,311 B1 * | 5/2001 | Levin et al. ............ 514/227.5 |
| 6,387,901 B1 | 5/2002 | Chupak et al. |
| 7,179,911 B2 | 2/2007 | Wang et al. |

FOREIGN PATENT DOCUMENTS

| WO | WO 97/20824 | 6/1997 |
| WO | WO 98/34918 | 8/1998 |
| WO | WO 03/037852 | 5/2003 |

OTHER PUBLICATIONS

Shire, M.G., et al., "TNF-alpha inhibitors and rheumatoid arthritis", *Exp. Opin. Ther. Patents*, 1998, 8(5):531-544.
Grossman, J.M., et al., "Rheumatoid arthritis: current clinical and research directions", *J. Women's Health*, , 1997, 6(6):627-638.
Isomaki, P. et al., "Pro- and anti-inflammatory cytokines in rheumatoid arthritis",*Ann. Med.*, 1997, 29(6):499-507.
Camussi, G., et al., "The future role of anti-tumour necrosis factor (TNF) products in the treatment of rheumatoid arthritis", *Drugs*, 1998, 55(5):613-620.
Van Assche, G., et al., "Anti-TNF agents in Crohn's disease", *Exp. Opin. Invesitig. Drugs*, 2000, 9(1):103-11.
Rutgeerts, P. et al., "Novel Therapies for Crohn's Disease", *Drugs of Today*, 2000, 36(Suppl. G.), 59-68.
Kreuger, G., et al., "Potential of tumor necrosis factor inhibitors in psoriasis and psoriatic arthritis", *Archives of Dermatology*, 2004, 140(2):218-25.
Kristensen, M., et al., "Localization of tumour necrosis factor-alpha (TNF-alpha) and its receptors in normal and psoriatic skin: epidermal cells express the 55-kD but not the 75-kD TNF receptor", *Clin. Exp. Immunol.*, 1993, 94(2)354-62.
Lorenz, H.M., et al., "Perspective for TNF-alpha-targeting therapies", *Arthritis Res.*, 2002, 4(supple 3), S17-S24.
Wendling, D., et al., "Anti-TNF-alpha therapy in ankylosing spondylitis", *Exp. Opin. Pharmacotherapy*, 2004, 5(7):1497-1507.
Mathison, J.C., et al., "Participation of Tumor Necrosis Factor in the Mediation of Gram Negative Bacterial Lipopolysaccharide-Induced Injury in Rabbits", *J. Clin. Invest.*, 1998, 81:1925-1937.
Miethke, et al., "T cell-mediated lethal shock triggered in mice by the superantigen staphylococcal enterotoxin B: critical role of tumor necrosis factor", *J. Exp. Med.*, 1992, 175:91-98.
Robertshaw, H.J., et al., Release of tumour necrosis factor alpha (TNFalpha) by TNFalpha cleaving enzyme (TACE) in response to septic stimuli in vitro, *Br. J. Anaesth.* , 2005, 94(2):222-228.
Piguet, P.F., "Tumor necrosis factor/cachectin in an effector of skin and gut lesions of the acute phase of graft-vs.-host disease", *J. Exp. Med.*, 1987, 166:1280-1289.
Beutler, B., et al., Tumor necrosis, cachexia, shock, and inflammation: a common mediator, *Ann. Rev. Biochem.*, 1988, 57:505-518.
Ksontini, R., et al., "Revisitng the role of Tumor Necrosis Factor alpha and the Response to Surgical Injury and Inflammation", *Arch. Surg.*, 1988, 133::558-567.
Packer, M., "Is tumor necrosis factor an important neurohormonal mechanism in chronic heart failure?", *Circulation*, 1995, 92(6):1379-1382.
Ferrari, R., et al., Tumor necrosis factor soluble receptors in patients with various degrees of congestive heart failure, *Circulation*, 1995, (92(6):1479-1486.
Feldman, A.M., The role of tumor necrosis Factor in the pathophysiology of heart failure:, *J. Am. Coll. Cardiol.*, 2003, 35:537.
Satoh, M.., et al., "Increased expression of tumor necrosis factor-alpha converting enzyme and tumor necrosis factor-alpha in peripheral blood mononuclear cells in patients with advanced congestive heart failure", *European J. Heart Failure*, 2004, 6:869-875.
Gilles, S., et al., "Release of TNF-alpha during myocardial reperfusion depends on oxidative stress and is prevented by mast cell stabilizers", *Cardiovascular Res.*, 2003, 60:608-616.
Moro, M.A., et al., "Expression and function of tumour necrosis factor-alpha-converting enzyme in the central nervous system", *Neurosignals*, 2003, 12:53-58.
Colon, A.L., et al., Implication of TNF-alpha convertase (TACE/ADAM17) in inducible nitric oxide synthase expression and inflammation in an experimental model of colitis, *Cytokine*, 2001, 16(6):220-226.

(Continued)

*Primary Examiner*—Kahsay T Habte
(74) *Attorney, Agent, or Firm*—Pepper Hamilton LLP

(57) ABSTRACT

This invention relates to crystalline polymorphs of (3S)-N-hydroxy4-({4-[(4-hydroxy-2-butynyl)oxy]phenyl}sulfonyl)-2,2-dimethyl-3-thiomorpholine carboxamide, and preparation and uses thereof.

27 Claims, 12 Drawing Sheets

OTHER PUBLICATIONS

Kirkegaard, T., et al., "Tumour necrosis factor-alpha converting enzyme (TACE) activity in human colonic epithelial cells",. *Clin. Exp. Immunol.*, 2004, 135(1):146-53.

Hotamisligil, G.S., et al., "Adipose expression of tumor necrosis factor-alpha: direct role in obesity-linked insulin resistance" *Science*, 1993, 259:87-91.

Hotamisligil, G.S., et al., "Tumor Necrosis Factor alpha: A Key Component of the Obesity-Diabetes Link", *Diabetes*, 1994, 43:1271-1276.

Morimoto, Y., et al., "KB-R7785, a novel matrix metalloproteinase inhibitor, exerts its antidiabetic effect by inhibiting tumor necrosis factor-alpha production", *Life Sci.*, 1997, 61(8):795-803.

Trifilieff, A., et al., "Pharmacological profile of PKF242-484 and PKF241-66, novel dual inhibitors of TNF-alpha converting enzyme and matrix metalloproteinases, in models of airway inflammation", *Brit. J. Pharmacol.*, 2002, 135(7):1655-64.

Wang, X. et al., "Inhibitor of Tumor Necrosis Factor-alpha-Converting Enzyme by a Selective Antagonist Protects Brain from Focal Ischemic Injury in Rats", *Mol. Pharmacol.* 2004, 65(4)896:890.

Wang, X., et al., Inhibition of Tumor Necrosis Factor-alpha Converting Enzyme by a Selective Small Molecular Antagonist Protects Brain from Thrombo-Embolic Ischemic Injury in Rat, *Circulation*, 2003, (Abstracts from Scientific Sessions - 17 Supp) IV-103.

Hallenbeck, J.M., "The many faces of tumor necrosis factor in stroke", *Nature Medicine*, 2002, 8(12):1363-1368.

Meli, D.N., et al., "In pneumococcal meningitis a novel water-soluble inhibitor of matrix metalloproteinases and TNF-alpha converting enzyme attenuates seizures and injury of the cerebral cortex", *J. Neuroimmunology*, 2004, 151::6-11.

Nelson, A.R., et al., "Matrix metalloproteinases: biologic activity and clinical implications", *J. Clin. Oncol.*, 2000, 18(5):1135-1149.

Clements, J.M., et al., "Matrix metalloproteinase expression during experimental autoimmune encephalomyelitis and effects of a combined matrix metalloproteinase and tumour necrosis factor-alpha inhibitor", *J. Neuroimmunol*. 1997, 74:85-94.

Peterson, P.K., et al., "Human cytomegalovirus-stimulated peripheral blood mononuclear cells induce HIV-1 replication via a tumor necrosis factor-alpha-mediated mechanism", *J. Clin. Invest.*, 1992, 89(2):574-580.

Pallares-Trujillo, J., et al., "TNF and AIDS: two sides of the same coin?", *Med. Res. Reviews*, 1995, 15(6):533-546.

Old, L. "Tumor necrosis factor (TNF)", *Science*, 1985, 230(4726):630-632.

Rankin, E.C., et al., "The therapeutic effects of an engineered human anti-tumour necrosis factor alpha antibody (CDP571) in rheumatoid arthritis.", *Br. J. Rheumatol.*, 1995, 34(4):334-342.

*Pharmaprojects*, 1996, Therapeutic Updates 17(Oct.) au197-M2Z.

McGeehan, G., et al., "TNF-alpha in Human Diseases", *Current Pharmaceutical Design*, 1996, 2:662-667.

*Remington's Pharmaceutical Sciences*, 17th ed., Ed. Alfonso R. Gennaro, Mack Publishing Co., Easton, Pa., 1985.

Sorbera, et al., "Prinomastat:oncolytic, matrix metalloprotase inhibitor", *Drugs of the Future*, 2000,. 25(2): 150-158.

Shirokova, E. et al, "Novel Acyclic Nucelotides and Nucleoside 5'-Triphosphates Imitating 2',3'-Dideoxy-2'3'-didehydronucleotides:Synthesis and Biological Properties", 1994, 37:3739-3748.

\* cited by examiner

CRYSTALLINE POLYMORPHS OF (3S)-N-HYDROXY-4-({4-[-(4-HYDROXY-2-BUTYNYL)OXY]PHENYL}SULFONYL)-2,2-DIMETHYL-3-THIOMORPHOLINE CARBOXAMIDE

CROSS REFERENCE TO RELATED APPLICATIONS

This application claims priority benefit of U.S. Provisional Application Ser. No. 60/577,784 filed Jun. 8, 2004, which is incorporated by reference herein in its entirety.

FIELD OF THE INVENTION

This invention relates to crystalline polymorphs of (3S)-N-hydroxy-4-({4-[(4-hydroxy-2-butynyl)oxy]phenyl}sulfonyl)-2,2-dimethyl-3-thiomorpholine carboxamide (apratastat), an inhibitor of TNF-α converting enzyme (TACE).

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. Exp. Opin. Ther. Patents 1998, 8(5), 531; Grossman, J. M.; Brahn, E. J. Women's Health 1997, 6(6), 627; Isomaki, P.; Punnonen, J. Ann. Med. 1997, 29, 499; Camussi, G.; Lupia, E. Drugs, 1998, 55(5), 613], Crohn's disease [Van Assche, G.; Rutgeerts, P.; Exp. Opin. Invest. Drugs, 2000, 9, 103; Rutgeerts, P.; Baert, F. Drugs of Today, 2000, 36(Suppl. G, Doctor in Focus), 59], psoriatic arthritis [Kreuger, G.; Callis, K.; Archives of Dermatology, 2004, 140, 218], psoriasis [Kristensen, M.; Chu, C. Q.; Eedy, D. J.; et al.; Clin. Exp. Immunol., 1993, 94, 354], vasculitis [Lorenz, H.-M.; Kalden, J. R.; Arthritis Res., 2002, 4(suppl 3), S17], ankylosing spondylitis [Wendling, D.; Toussirot, E.; Exp. Opin. Pharmacotherapy, 2004, 5, 1497], septic shock [Mathison, et. al. J. Clin. Invest. 1988, 81, 1925; Miethke, et. al. J. Exp. Med. 1992, 175, 91; Robertshaw, H. J.; Brennan, F. M.; Br. J. Anaesth., 2005, 94, 222], graft rejection [Piguet, P. F.; Grau, G. E.; et al. J. Exp. Med. 1987, 166, 1280], cachexia [Beutler, B.; Cerami, A. Ann. Rev. Biochem. 1988, 57, 505], anorexia, inflammation [Ksontini, R.; MacKay, S. L. D.; Moldawer, L. L. Arch. Surg. 1998, 133, 558], congestive heart failure [Packer, M. Circulation, 1995, 92(6), 1379; Ferrari, R.; Bachetti, T.; et. al. Circulation, 1995, 92(6), 1479; Feldman, A. M.; Combes, A.; Wagner, D.; J. Am. Coll. Cardiol., 2003, 35, 537; Mamoru, S.; Iwasaka, J.; Nakamura, M.; et al.; Eur. J. Heart Failure, 2004, 6, 869], post-ischaemic reperfusion injury [Gilles, S.; Zahler, S.; Welsch, U.; et al.; Cardiovascular Res., 2003, 60, 608], inflammatory disease of the central nervous system [Moro, M. A.; Hurtado, O.; Cardenas, A; et al.; Neurosignals, 2003, 12, 53], inflammatory bowel disease and ulcerative colitis [Colon, A. L.; Menchen, L. A.; Hurtado, O.; De Cristobal, J.; Lizasoain, I.; Leza, J. C.; Lorenzo, P.; Moro, M. A.; Cytokine, 2001, 16, 220; Kirkegaard, T.; Pedersen, G.; Saermark, T.; Brynskov, J.; Clin. Exp. Immunol.; 2004, 135, 146], insulin resistance and diabetes [Hotamisligil, G. S.; Shargill, N. S.; Spiegelman, B. M.; et. al. Science, 1993, 259, 87; Hotamisligil, G. S.; Spiegelman, B. M.; Diabetes, 1994, 43, 1271; Morimoto, Y.; Nishikawa, K.; Ohashi, M. Life Sci., 1997, 61, 795], chronic obstructive pulmonary disease (COPD) and asthma [Trifilieff, A.; Walker, C.; Keller, T.; Kottirsch; Neumann, U.; Brit. J. Pharmacol., 2002, 135, 1655], stroke [Wang, X.; Feuerstein, G. Z.; Xu, L.; et al.; Mol. Pharmacol., 2004, 65, 890; Wang, X.; Xu, L.; Feuerstain, G. Z.; et al. Circulation, 2003, 108 (17 Supp.), iv-103; Hallenback, J. M.; Nature Medicine, 2002, 8, 1363.], pneumococcal meningitis [Meli, D. N.; Loeffler, J. M.; Baumann, P. et al.; J. Neuroimmunology, 2004, 151, 6], tumor metastasis [Nelson, A. R.; Fingleton, B.; Rothenberg, M. L.; et al.; J. Clin. Oncol., 2000, 18, 1135], multiple sclerosis [Clements, J. M.; Cossins, J. A.; Wells, G. M.; et al.; J. Neuroimmunol., 1997, 74, 85]] and HIV infection [Peterson, P. K.; Gekker, G.; et al. J. Clin. Invest 1992, 89, 574; Pallares-Trujillo, J.; Lopez-Soriano, F. J. Argiles, J. M. Med. Res. Reviews, 1995, 15 (6), 533], in addition to its well-documented antitumor properties [Old, L. Science, 1985, 230, 630]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. Br. J. Rheumatol. 1995, 34, 334; Pharmaprojects, 1996, Therapeutic Updates 17 (October), au197-M2Z]. This observation has been extended to humans as well ["TNF-α in Human Diseases", Current Pharmaceutical Design, 1996, 2, 662].

(3S)-N-hydroxy-4-({4-[(4-hydroxy-2-butynyl)oxy]phenyl}sulfonyl)-2,2-dimethyl-3-thiomorpholinecarboxamide (apratastat) is a potent, reversible, and competitive inhibitor of TACE in vitro having the structure below:

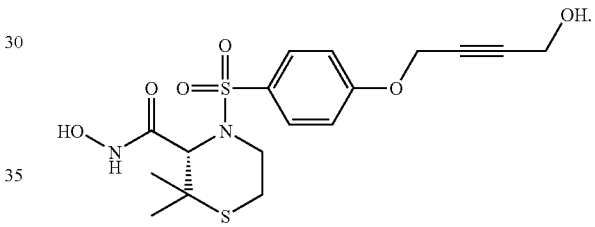

Apratastat inhibits TNF-α secretion by human synovium tissue explants from patients suffering from rheumatoid arthritis and is a potent TNF-α inhibitor in murine and primate lipopolysaccharide (LPS) models. These data demonstrate that apratastat has the potential for treating and/or inhibiting disease states mediated by TACE. The preparation of apratastat was first disclosed in U.S. Pat. No. 6,225,311, the entire disclosure of which is hereby incorporated by reference.

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. In cases where two or more polymorph substances can be produced, it is desirable to have a method to make polymorphs in pure form. In deciding which polymorph is preferable, the numerous properties of the polymorphs must be compared and the preferred polymorph chosen based on the many physical property variables. It is entirely possible that one polymorph form can be preferable in some circumstances where certain aspects such as ease of preparation, stability, etc. are deemed to be critical. In other situations, a different polymorph may be preferred, for example, for greater solubility and/or superior pharmacokinetics.

Because improved drug formulations showing, for example, better bioavailability or better stability are consistently sought, there is an ongoing need for new or purer polymorphic forms of drug molecules. The polymorphs of apratastat described herein help meet these and other needs.

SUMMARY OF THE INVENTION

The present invention provides crystalline polymorphs of (3S)-N-hydroxy-4-({4-[(4-hydroxy-2-butynyl)oxy] phenyl}sulfonyl)-2,2-dimethyl-3-thiomorpholinecarboxamide (apratastat) characterized by the powder X-ray diffraction data, IR data, and Raman spectroscopy data provided herein. Compositions containing the polymorphs of apratastat are also provided. The invention further provides methods of preparing the apratastat polymorphs.

Methods of treating or inhibiting diseases or disorders mediated by TACE are also provided by the present invention, comprising administering to a mammal a therapeutically effective amount of a composition containing a polymorph of apratastat as described herein. The invention further provides methods of alleviating a symptom of a disease or disorder mediated by TNF-α comprising administering to a mammal a therapeutically effective amount of a composition containing a polymorph of apratastat as described herein.

DETAILED DESCRIPTION OF THE INVENTION

The invention provides crystalline polymorphs of (3S)-N-hydroxy-4-({4-[(4-hydroxy-2-butynyl)oxy] phenyl}sulfonyl)-2,2-dimethyl-3-thiomorpholinecarboxamide (apratastat) which can be identified by one or more solid state analytical methods.

Figure 1:
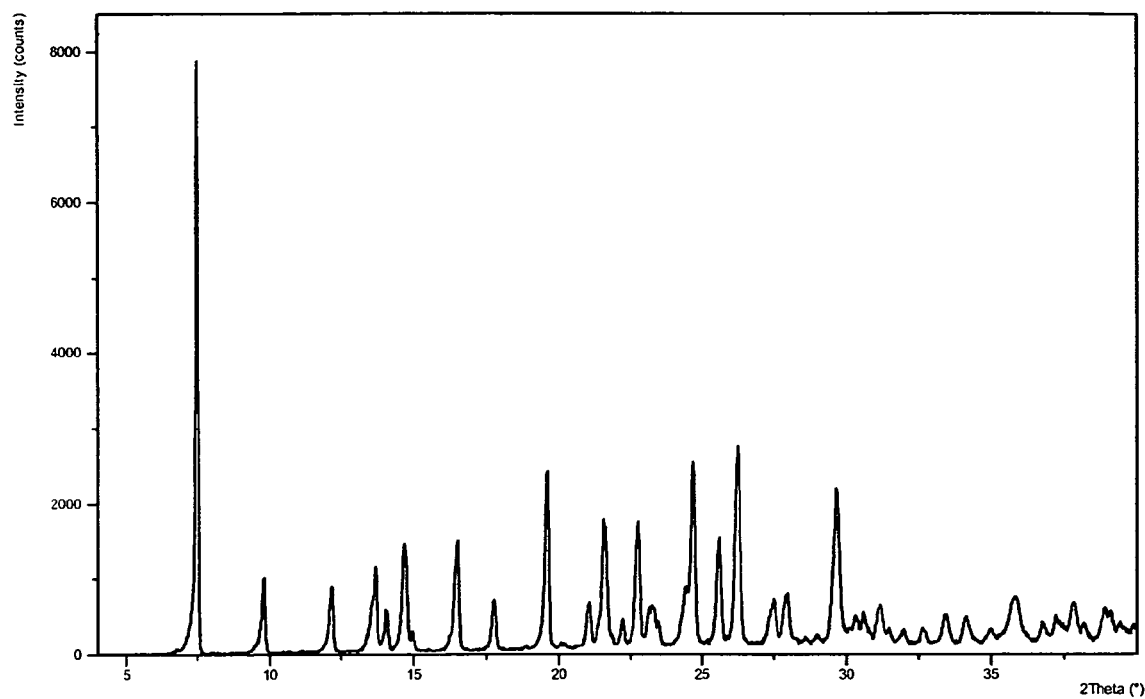
FIG. 1 depicts a powder X-ray diffration pattern of apratastat polymorph form A.

One polymorph (form A) can be identified by its powder X-ray diffraction pattern, for example, as shown in FIG. 1. Powder X-ray diffraction data consistent with form A is provided in Table 1 below.

TABLE 1

| Degree (2θ) | Intensity |
|---|---|
| 6.8 | 58.6 |
| 7.5 | 7827.4 |
| 9.8 | 968.1 |
| 12.2 | 882.2 |
| 13.7 | 1058.2 |
| 14.1 | 521.5 |
| 14.7 | 1395.2 |
| 14.9 | 256.2 |
| 15.3 | 80.1 |
| 16.5 | 1387.6 |
| 17.8 | 669.9 |
| 18.9 | 65.2 |
| 19.6 | 2304.3 |
| 20.1 | 85.1 |
| 21.0 | 593.3 |
| 21.6 | 1599.8 |
| 22.2 | 364.5 |
| 22.7 | 1523.9 |
| 23.3 | 523.8 |
| 23.4 | 313.6 |
| 24.5 | 740.8 |
| 24.7 | 2384.0 |
| 25.6 | 1325.3 |
| 26.2 | 2530.8 |
| 27.5 | 576.7 |
| 28.0 | 643.8 |
| 28.6 | 90.5 |
| 29.0 | 131.0 |
| 29.7 | 1871.3 |
| 30.3 | 355.5 |
| 30.6 | 372.5 |
| 31.1 | 493.3 |
| 31.5 | 180.5 |
| 32.0 | 203.1 |
| 32.7 | 199.1 |
| 33.5 | 376.1 |
| 34.2 | 340.6 |
| 35.0 | 184.6 |
| 35.8 | 614.9 |
| 36.8 | 253.9 |
| 37.2 | 357.8 |
| 37.8 | 535.2 |
| 38.2 | 258.7 |
| 38.9 | 478.5 |
| 39.1 | 375.7 |
| 39.4 | 233.1 |
| 39.9 | 207.4 |

Polymorph form A of apratastat is characterized as having peaks in its powder X-ray diffraction pattern at diffraction angle 2θ of about 7.5°, 19.6°, 24.7°, and 26.2°. Form A may be further characterized as having peaks at diffraction angle 2θ of about 14.7°, 16.5°, 21.6°, 22.7°, 25.6° and 29.7°. Due to variations in sample preparation and instrument configurations, all reported powder X-ray diffraction peaks may vary by plus or minus 0.2°.

Figure 2:
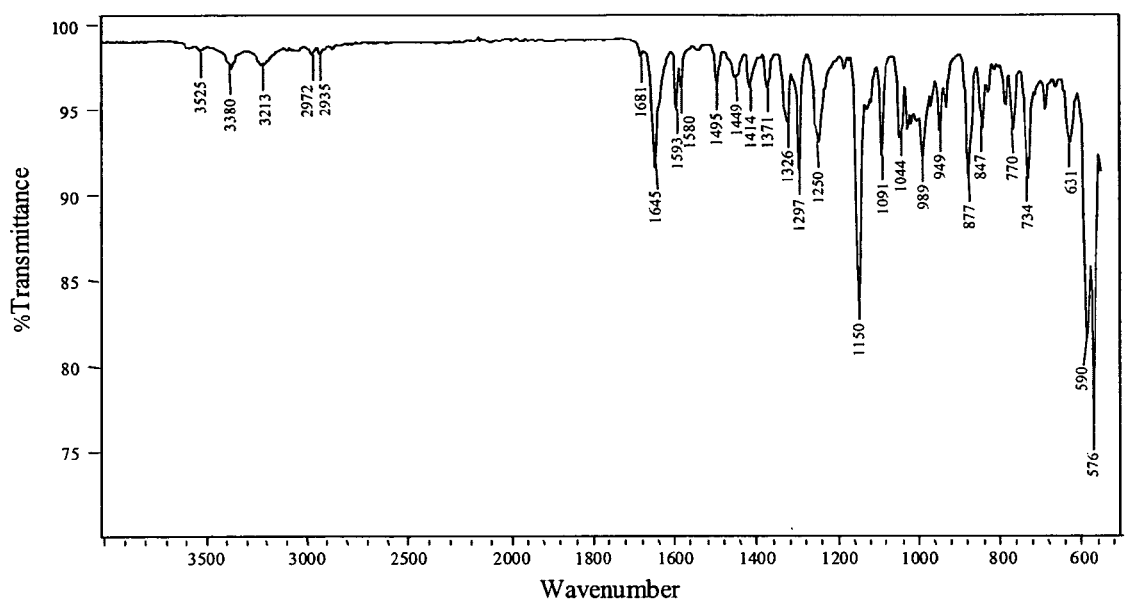
FIG. 2 depicts an attentuated total reflection infrared spectrum of apratastat polymorph form A.
Figure 3:
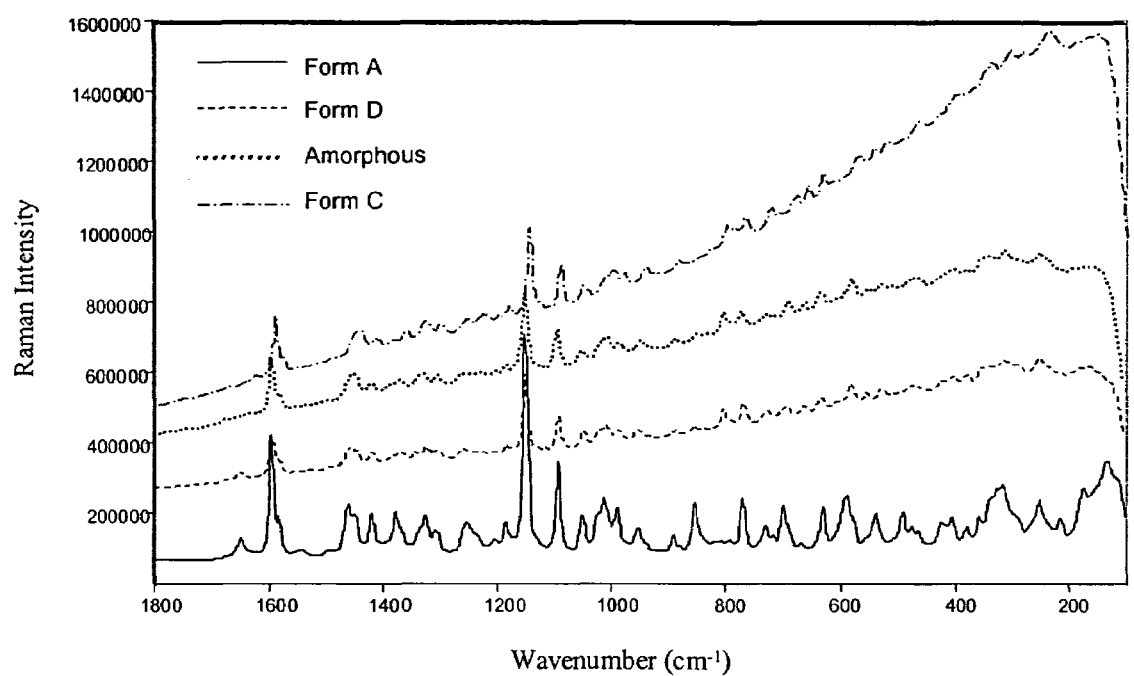
FIG. 3 depicts Raman spectra of apratastat polymorph forms A, C and D and an amorphous form of apratastat.

Form A can also be identified by its infrared (IR) spectrum, for example, as shown in FIG. 2. Form A can be characterized as having one or more bands in its IR spectrum at about 3380 $cm^{-1}$, 3220 $cm^{-1}$, 2970 $cm^{-1}$, 2930 $cm^{-1}$, 1680 $cm^{-1}$, 1650 $cm^{-1}$, 1590 $cm^{-1}$, 1580 $cm^{-1}$, 1500 $cm^{-1}$, 1450 $cm^{-1}$, 1370 $cm^{-1}$, 1330 $cm^{-1}$, 1300 $cm^{-1}$, 1250 $cm^{-1}$, 1150 $cm^{-1}$, 1090 $cm^{-1}$, and 1050 $cm^{-1}$. Due to variations in sample preparation and instrument configurations, all IR bands may vary by as much as plus or minus 15 $cm^{-1}$ (e.g., plus or minus 15 $cm^{-1}$, plus or minus 10 $cm^{-1}$, or plus or minus 5 $cm^{-1}$). Form A can further be identifed by its Raman spectrum, for example, as shown in FIG. 3.

Apratasat polymorph form A can be prepared, for example, by recrystallizing apratastat (made, for example, according to the procedue set forth in U.S. Pat. No. 6,225,311, which is incorporated by reference herein in its entirety) from a suitable solvent or solvent mixture. Weight ratios of the total solvent to the amount of apratastat can be, for example, about 5:1, about 4:1, about 3:1, about 2:1, or about 1:1. Examples of suitable solvents include alcohols such as methanol, ethanol, n-propanol, isopropanol, and mixtures thereof. Water may be added as a co-solvent to any of the aforementioned alcohols to form a solvent mixture, e.g., methanol/water, ethanol/water, n-propanol/water, or isopropanol/water mixtures. The apratastat solution or suspension may be heated for a time sufficient to produce form A. For example, the solution or suspension may be heated to a temperature between about 25° C. and the reflux temperature of the solvent or solvent mixture. For an isopropanol or isopropanol/water solution, suitable temperatures may range from about 25° C. to about 80° C. (e.g., about 30° C. to about 80° C., or about 50° C. to about 75° C.). After heating, the solution may optionally be cooled to a temperature at or below 25° C. (e.g., about −5° C. to about 25° C., about 0° C. to about 20° C., about 0° C. to about 15° C., or about 0° C. to about 10° C.). Form A seed crystals, obtained from a previous preparation, may optionally be added during the cooling process. Additional water may be added to facilitate precipitation of the polymorph form A. Alternatively, an alcohol solution of apratastat may be slowly evaporated at or near ambient temperature (e.g., 20-25° C.) to form a slurry, which can then be filtered and dried to yield the desired polymorph. In addition to the parameters described above, those of skill in the art of will readily recognize other suitable recrystallization conditions that can yield essentially the same results.

Figure 4:
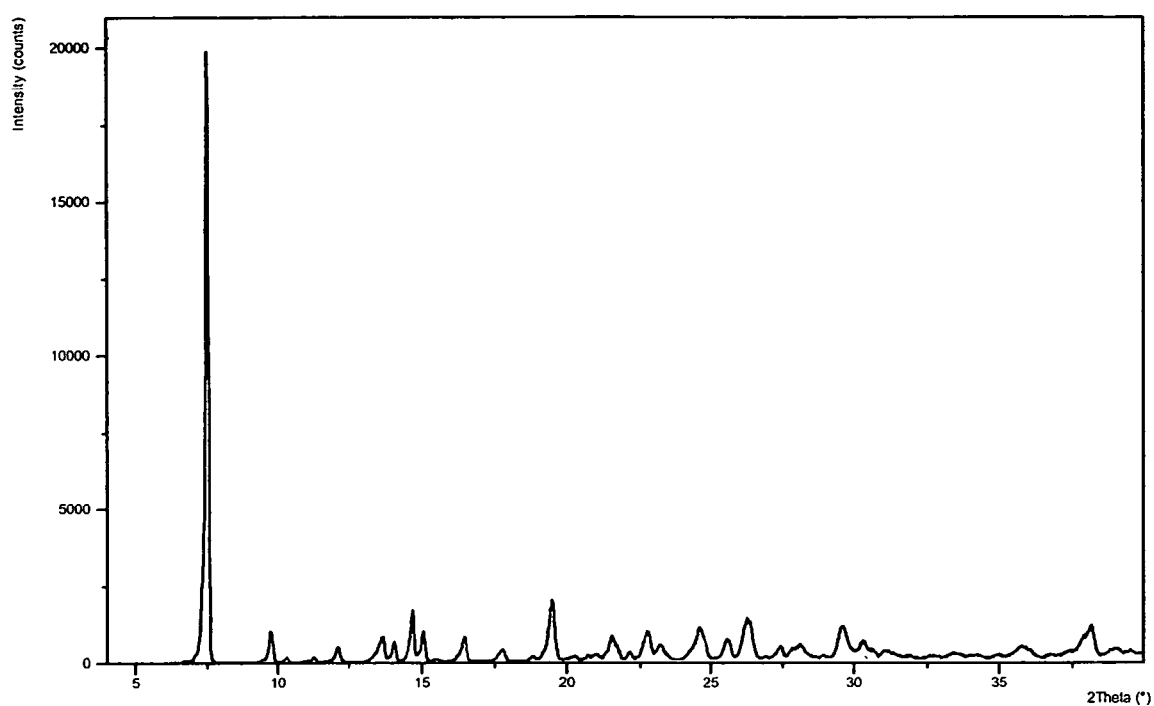
FIG. 4 depicts a powder X-ray diffration pattern of apratastat polymorph form B.

If apratastat polymorph form A is placed in a low-moisture environment (for example, about 4-5% relative humidity) at or near room temperature, a portion or all of the polymorph may convert to a new form (form B), which can be identified by its powder X-ray diffraction pattern as shown in FIG. 4. Powder X-ray diffraction data consistent with form B is provided in Table 2 below.

TABLE 2

| Degree (2θ) | Intensity |
| --- | --- |
| 7.6 | 9466.6 |
| 9.8 | 678.8 |
| 10.4 | 271.0 |
| 11.1 | 113.4 |
| 11.3 | 113.9 |
| 12.2 | 394.2 |
| 13.5 | 457.0 |
| 13.7 | 963.2 |
| 14.1 | 964.1 |
| 14.7 | 1115.6 |
| 15.1 | 685.3 |
| 15.6 | 201.7 |
| 16.6 | 887.0 |
| 17.9 | 546.5 |
| 19.0 | 248.3 |
| 19.5 | 1427.2 |
| 20.3 | 333.2 |
| 20.8 | 147.9 |
| 21.2 | 138.6 |
| 21.8 | 841.2 |
| 22.2 | 456.1 |
| 22.9 | 1251.3 |
| 23.3 | 680.5 |
| 24.6 | 771.1 |
| 24.8 | 776.0 |
| 25.7 | 729.0 |
| 26.4 | 1469.9 |
| 27.0 | 127.4 |
| 27.5 | 233.5 |
| 28.2 | 585.3 |
| 29.0 | 196.4 |
| 29.2 | 86.4 |
| 29.8 | 1031.8 |
| 30.4 | 498.2 |
| 30.8 | 351.1 |
| 31.3 | 193.5 |
| 31.6 | 130.8 |
| 33.0 | 269.0 |
| 33.4 | 87.3 |
| 33.8 | 128.7 |
| 34.3 | 146.7 |
| 35.1 | 145.5 |
| 36.0 | 391.7 |
| 36.9 | 129.2 |
| 37.6 | 279.4 |
| 38.3 | 968.6 |
| 39.0 | 208.9 |
| 39.2 | 307.8 |
| 39.6 | 337.0 |

Polymorph form B of apratastat is characterized as having peaks in its powder X-ray diffraction pattern at diffraction angle 2θ of, for example, about 7.6°, 19.5°, 22.9°, and 26.4°. The powder X-ray diffraction pattern for form B contains several peaks not present in that of form A, for example, peaks at 10.4°, 11.1° and 11.3°. Due to variations in sample preparation and instrument configurations, all reported powder X-ray diffraction peaks may vary by plus or minus 0.2°.

Polymorph form B is likely also an anhydrous form of apratastat. The powder X-ray diffraction data for forms A and B are similar, and no significant differences are expected in the physical properties (e.g., solubility) of form A and form B. Form B can convert back to form A under ambient conditions with little or no energy input. Form B disappears upon mild heating (e.g., at or above about 35° C.) under ambient humidity levels.

Figure 5:
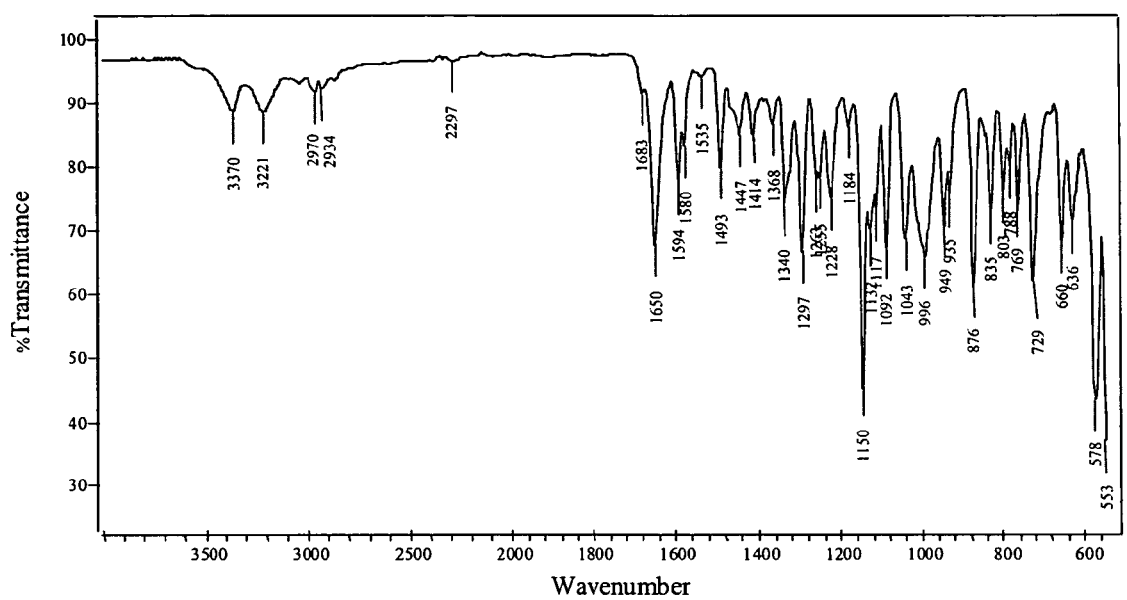
FIG. 5 depicts an attentuated total reflection infrared spectrum of apratastat polymorph form C.
Figure 6:
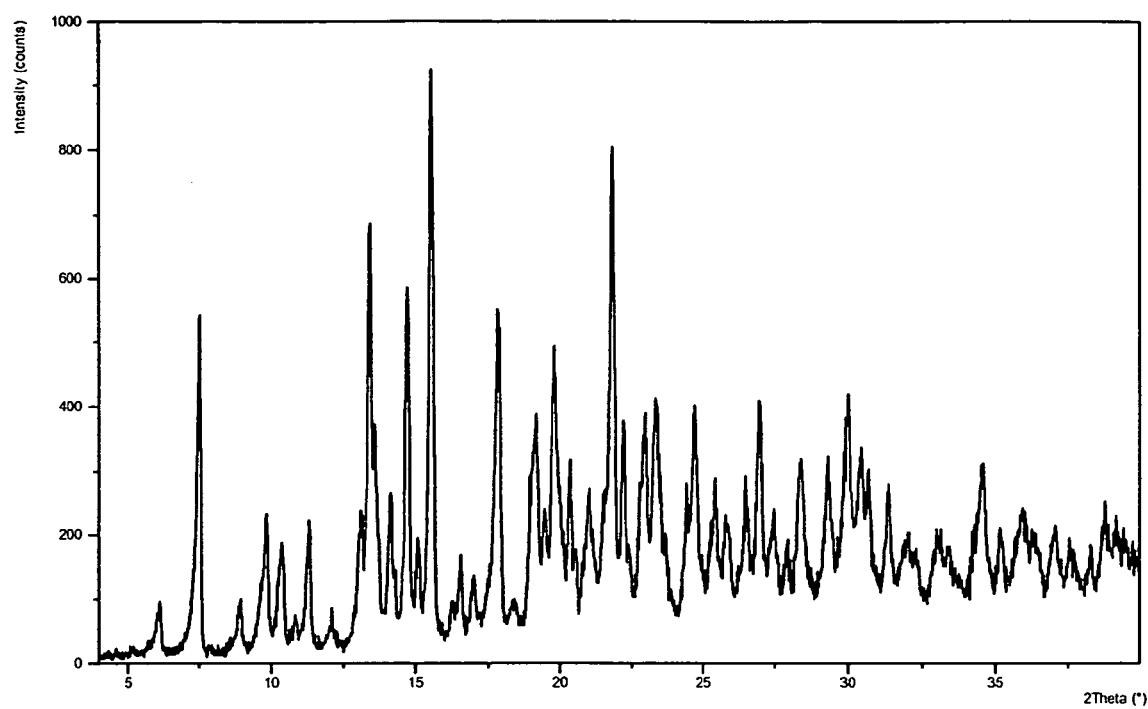
FIG. 6 depicts a powder X-ray diffration pattern of apratastat polymorph form C.

A third anhydrous crystalline polymorph of apratastat (form C) can form when apratastat is heated at or near about 120° C., but not exceeding about 145° C. Form C can be identified by its IR spectrum, for example, as shown in FIG. 5, and its Raman spectrum, for example, as shown in FIG. 3. Form C can also be identified by its powder X-ray diffraction pattern as shown in FIG. 6 and in Table 3 below.

TABLE 3

| Degree (2θ) | Intensity |
| --- | --- |
| 6.1 | 71.0 |
| 7.5 | 472.3 |
| 8.9 | 84.9 |
| 9.9 | 208.1 |
| 10.4 | 131.2 |
| 10.9 | 44.9 |
| 11.3 | 137.3 |
| 12.1 | 47.4 |
| 13.1 | 192.4 |
| 13.4 | 599.5 |
| 13.6 | 284.6 |
| 14.1 | 196.6 |
| 14.7 | 449.6 |
| 15.1 | 109.1 |
| 15.5 | 691.4 |
| 16.3 | 74.7 |
| 16.5 | 116.3 |
| 17.0 | 86.4 |
| 17.8 | 476.1 |
| 16.4 | 69.4 |
| 19.1 | 285.9 |
| 19.5 | 190.5 |

TABLE 3-continued

| Degree (2θ) | Intensity |
|---|---|
| 19.8 | 390.7 |
| 20.3 | 232.4 |
| 20.5 | 107.3 |
| 21.0 | 185.0 |
| 21.8 | 606.6 |
| 22.2 | 250.1 |
| 22.9 | 281.0 |
| 23.3 | 344.4 |
| 24.4 | 182.1 |
| 24.7 | 320.7 |
| 25.4 | 174.7 |
| 25.8 | 135.5 |
| 26.2 | 61.1 |
| 26.5 | 160.8 |
| 27.0 | 302.3 |
| 27.4 | 142.4 |
| 27.9 | 80.6 |
| 28.4 | 215.2 |
| 29.3 | 176.9 |
| 30.0 | 268.7 |
| 30.5 | 256.0 |
| 30.7 | 171.0 |
| 31.3 | 151.1 |
| 32.0 | 94.7 |
| 32.3 | 57.8 |
| 33.1 | 104.0 |
| 33.4 | 75.6 |
| 33.7 | 54.9 |
| 34.6 | 207.9 |
| 35.2 | 105.0 |
| 35.9 | 114.6 |
| 36.4 | 89.6 |
| 37.0 | 85.4 |
| 37.7 | 77.5 |
| 38.2 | 81.9 |
| 38.8 | 106.3 |
| 39.2 | 86.8 |
| 39.5 | 59.2 |
| 39.9 | 45.6 |

Polymorph form C of apratastat is characterized as having peaks in its powder X-ray diffraction pattern at diffraction angle 2θ of, for example, about 7.5°, 13.4°, 15.5°, 17.8°, and 21.8°. Due to variations in sample preparation and instrument configurations, all reported powder X-ray diffraction peaks may vary by plus or minus 0.2°.

Figure 7:
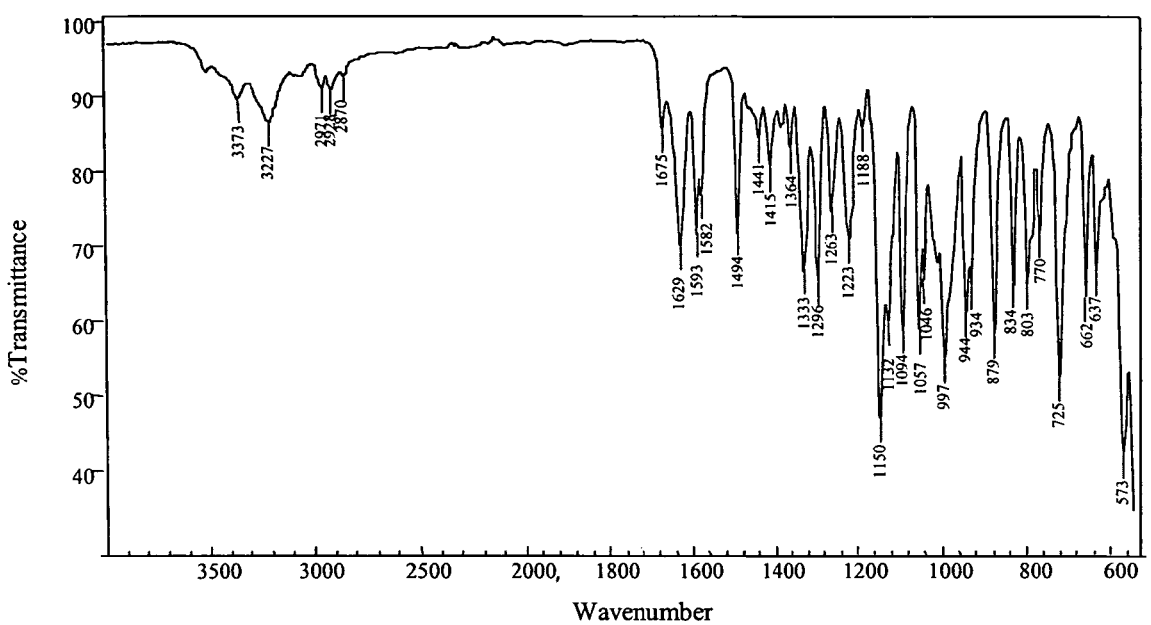
FIG. 7 depicts an attentuated total reflection infrared spectrum of apratastat polymorph form D.

A fourth anhydrous crystalline polymorph of apratastat (form D) can form when apratastat is heated above about 120° C., but not exceeding about 155° C. Form D can be identified by its IR spectrum, for example, as shown in FIG. 7, as well as its Raman spectrum, as shown in FIG. 3. Powder X-ray diffraction data consistent with form D is provided in FIG. 8 and in Table 4 below.

TABLE 4

| Degree (2θ) | Intensity |
|---|---|
| 8.3 | 647.8 |
| 9.2 | 49.9 |
| 9.5 | 175.9 |
| 10.1 | 128.7 |
| 10.7 | 26.9 |
| 11.1 | 29.6 |
| 12.4 | 106.7 |
| 12.6 | 147.5 |
| 12.8 | 232.2 |
| 13.5 | 437.5 |
| 13.6 | 540.2 |
| 13.9 | 643.1 |
| 14.1 | 225.6 |
| 14.5 | 28.3 |
| 14.8 | 145.5 |
| 15.1 | 156.0 |
| 15.5 | 334.7 |
| 15.8 | 258.8 |
| 16.1 | 107.2 |
| 16.4 | 207.9 |
| 16.6 | 69.9 |
| 17.0 | 124.7 |
| 17.2 | 443.2 |
| 17.8 | 119.0 |
| 18.5 | 948.7 |
| 19.0 | 659.8 |
| 19.5 | 429.6 |
| 19.8 | 87.8 |
| 20.3 | 346.4 |
| 20.6 | 1115.6 |
| 21.2 | 578.3 |
| 21.6 | 205.7 |
| 21.8 | 122.1 |
| 22.3 | 102.9 |
| 22.8 | 82.9 |
| 23.6 | 56.1 |
| 24.4 | 227.1 |
| 24.9 | 783.1 |
| 25.4 | 225.0 |
| 25.8 | 142.6 |
| 26.2 | 118.7 |
| 26.7 | 237.7 |
| 27.0 | 112.1 |
| 27.6 | 148.1 |
| 28.0 | 217.8 |
| 28.5 | 677.1 |
| 28.8 | 191.5 |
| 29.1 | 121.3 |
| 29.6 | 53.2 |
| 30.0 | 198.9 |
| 30.7 | 85.7 |
| 31.4 | 84.9 |
| 32.0 | 106.9 |
| 32.3 | 132.7 |
| 32.9 | 220.0 |
| 33.7 | 71.6 |
| 34.0 | 103.3 |
| 34.4 | 153.8 |
| 34.9 | 279.6 |
| 35.8 | 99.7 |
| 36.4 | 108.8 |
| 36.7 | 134.1 |
| 37.6 | 158.4 |
| 38.0 | 167.5 |
| 38.3 | 66.4 |
| 38.6 | 117.0 |
| 39.0 | 109.5 |
| 39.3 | 113.8 |

Polymorph form D of apratastat is characterized as having peaks in its powder X-ray diffraction pattern at diffraction angle 2θ of, for example, about 8.3°, 18.5°, 19.0°, 20.6°, 24.9°, and 28.5°. Due to variations in sample preparation and instrument configurations, all reported powder X-ray diffraction peaks may vary by plus or minus 0.2°.

Figure 9:
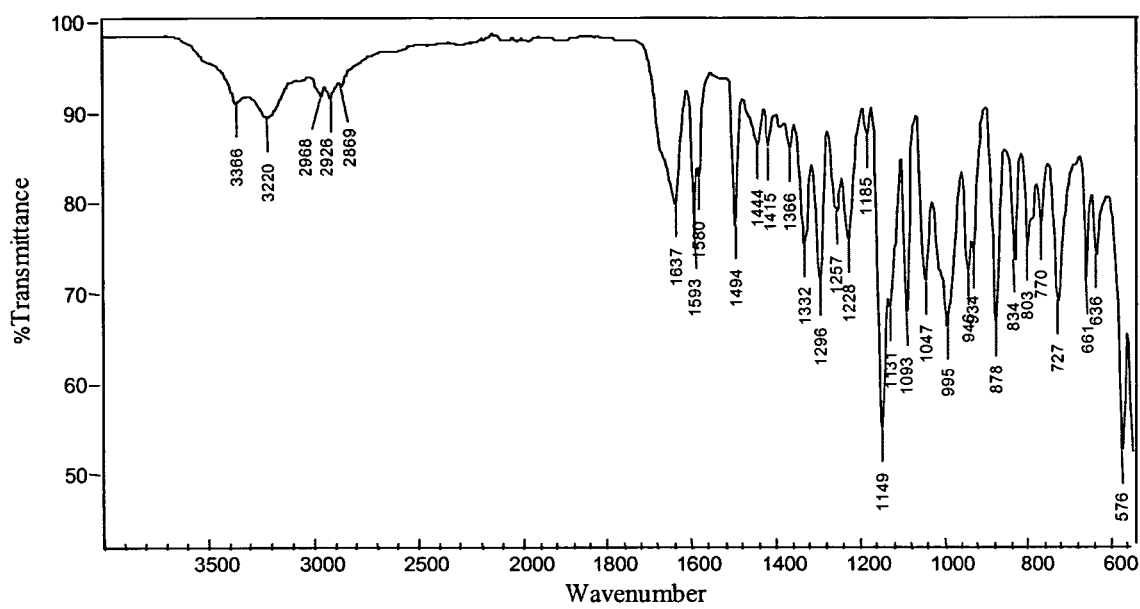
FIG. 9 depicts an attentuated total reflection infrared spectrum of an amorphous form of apratastat.

Apratastat can also exist in an amorphous form. For example, prolonged and/or intense heating (e.g., at or above about 155° C.), or heating in the presence of oxygen can facilitate formation of the amorphous form of apratastat. An IR spectrum of a representative amorphous form of apratastat is shown in FIG. 9, and a representative Raman spectrum is shown in FIG. 3.

Figure 10:
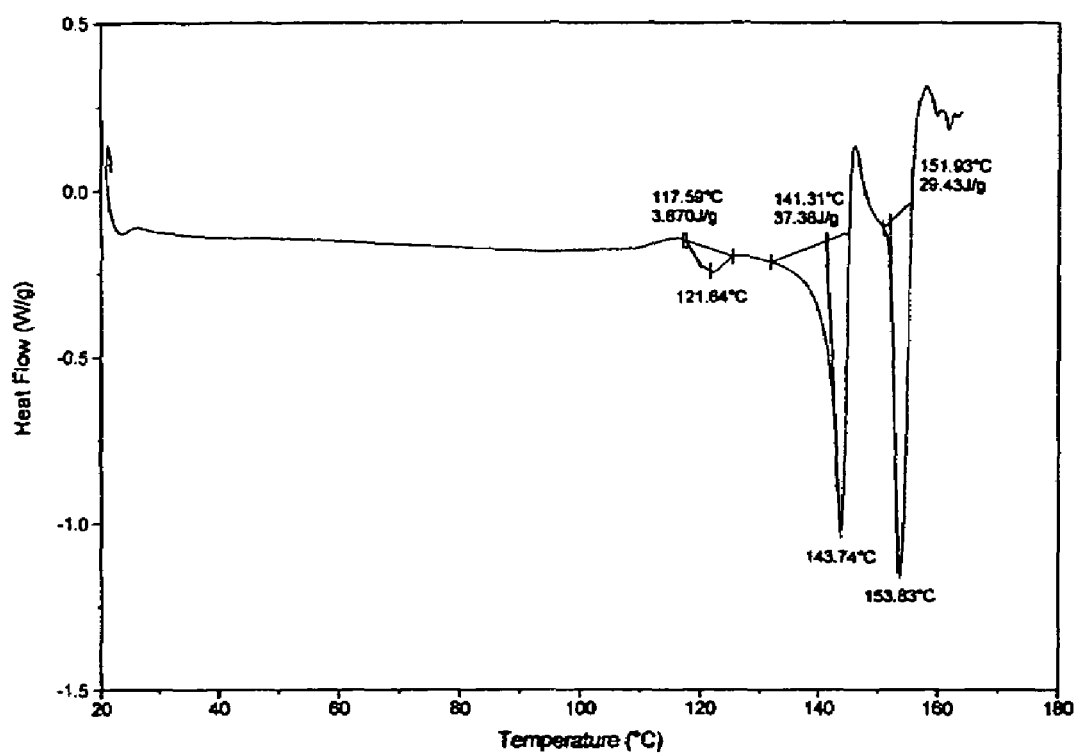
FIG. 10 depicts a differential scanning calorimetry profile of a sample of apratastat polymorph form A.

Differential scanning calorimetry (DSC) experiments on apratastat polymorph A have revealed three endotherms at about 121° C., 144° C. and 154° C. (FIG. 10). It is believed that the endotherm at about 144° C. is related to the transformation from form C to amorphous and/or to form D, and the 154° C. endotherm is the melting event of form D. The broad endotherm which generally occurs between about 100° C. and about 125° C. (which sometimes appears as an exo-endotherm) is thought to be related to the transformation of A to other forms. All three endotherms do not always appear in DSC experiments, however, and the extent of the transformation from form A to forms B, C or D, or the amorphous state appears to depend on many parameters, such as humidity, ambient oxygen levels, temperature, intensity of heating, heating scheme, and sample history and characteristics (e.g., moisture content and particle size). The DSC experiments indicate that upon heating, the first crystalline transformation tends to be to form C whether in an inert atmosphere or with a limited amount of oxygen present, but form C generally does not exist at temperatures higher than about 145° C. If the transformation to form D does occur, it tends to prevail over the transformation to form C at higher temperatures and longer heating times. Form D generally does not exist at temperatures higher than about 155° C.

As described in U.S. Pat. No. 6,225,311, apratastat is an inhibitor of matrix metalloproteinase (MMP) and TACE enzymes. Apratastat is therefore useful in the treatment or prevention of disorders mediated by one or more of the MMP enzymes and/or TACE, such as arthritis, tumor metastasis, tissue ulceration, abnormal wound healing, periodontal disease, graft rejection, insulin resistance, bone disease, septic shock, congestive heart failure and HIV infection and for the alleviation of symptoms thereof. Apratastat is also useful in treating or inhibiting pathological changes mediated by MMP enzymes such as atheroscerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the central nervous system, cirrhosis of the liver, glomerular disease of the kidney, premature rupture of fetal mambranes, inflammatory bowel disease, age related macular degenereation, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection and for the alleviation of symptoms thereof. Accordingly, polymorphs of apratastat and compositions containing such polymorphs can be used to treat or prevent these diseases and disorders. Methods of treatment include identifying a mammal having a disease or disorder mediated by TNF-α, and providing to the mammal a composition containing a therapeutically effective amount of a polymorph of apratastat as described herein.

In further embodiments, the methods are provided for alleviating a symptom of a disease or disorder mediated by TNF-α. In some embodiments, the methods include identifying a mammal having a symptom of a disease or disorder mediated by TNF-α, and providing to the mammal an amount of a composition containing a polymorph of apratastatas described herein effective to ameliorate (i.e., lessen the severity of) the symptom.

The present invention provides pharmaceutical compositions comprising at least one polymorph according to the invention and one or more pharmaceutically acceptable carriers, excipients, or diluents. In some embodiments, the composition contains at least about 50% to at least about 99% by weight of a single polymorph (e.g., at least about 50%, 55%, 60%, 65%, 70%, 75%, 80%, 85%, 90%, 95%, 96%, 97%, 98%, or 99%). Examples of suitable carriers are well known to those skilled in the art and are prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable. Supplementary active ingredients can also be incorporated into the compositions.

The compositions of the invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. The compositions may be formulated in conventional manner, for example, in a manner similar to that used for known antiinflammatory agents. Oral formulations may comprise any conventionally used oral form, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets may contain up to 99% of the active ingredient.

Capsules may contain mixtures of the polymorph with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The polymorphs of this invention can be dissolved or suspended in a pharmaceutically acceptable liquid carrier such as water, an organic solvent, or a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Examples of liquid carriers for oral and parenteral administration include water (particularly containing additives as described above, e.g. cellulose derivatives, such as a sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compositions of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compositions directly to the airways in the form of an aerosol. For administration by intranasal or intrabrochial inhalation, the compounds of this invention may be formulated into an aqueous or partially aqueous solution.

The polymorphs according to the invention or compositions containing the polymorphs may be administered parenterally or intraperitoneally. Solutions or suspensions of these compositions may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The polymorphs of this invention may be administered transdermally, i.e., administered across the surface of the body and the inner linings of bodily passages including epithelial and mucosal tissues. Such administrations may be carried out using the present compositions in lotions, creams, foams, patches, suspensions, solutions, and suppositories (rectal and vaginal). Topical formaulations that deliver the compositions through the epidermis may be useful for localized treatment of inflammation and arthritis.

Transdermal administration may be accomplished through the use of a transdermal patch containing the active composition and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The polymorphs of this invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

Lipid formulations or nanocapsules may be used to introduce the compositions of the present invention into host cells either in vitro or in vivo. Lipid formulations and nanocapsules may be prepared by methods known in the art.

In order to increase the effectiveness of the compositions of the present invention, it may be desirable to combine these compositions with other agents effective in the treatment of the target disease. For inflammatory diseases, other agents effective in their treatment, and particularly in the treatment of rheumatoid arthritis, may be administered with the compounds of the present invention. The other agents may be administered at the same time or at different times than the compositions of the present invention.

EXAMPLES

The following examples are presented to illustrate certain embodiments of the present invention, but should not be construed as limiting the scope of this invention.

Example 1

Preparation of Polymorph Form A

Crude (3S)-N-hydroxy-4-({4-[(4-hydroxy-2-butynyl)oxy]phenyl}sulfonyl)-2,2-dimethyl-3-thiomorpholinecarboxamide (105 g) was added to a mixture of 368 mL of isopropanol and 158 mL of water. The mixture was warmed to 51-55° C. until all solids had dissolved and a clear solution was obtained. Water (1.2 L) was added slowly over 1 hour, maintaining the temperature between 51 and 55° C. The solution was stirred at 51-55° C. for 3 hours, then allowed to cool gradually to 22-24° C. and stirred for an additional 12-16 hours. The solution was then cooled to 5-10° C. and stirred for 1 hour. The precipitated solids were filtered and dried in an oven at 50° C. for 72 hours under vacuum to yield 93 g product (85% yield). LC area % 99.3, KF 1.0%, IPA 0.5%; DSC: $T_{apex}$ 145° C.; $^1$H NMR (CD$_3$OD): δ1.45 (d, 6H), 2.52 (m, 1H), 3.07 (m, 2H), 3.9 (m, 2H), 4.14 (s,2H), 4.37 (s, 2H), 7.12 (d,2H), 7.71 (d, 2H); HPLC: area 99%, strength 98%.

Example 2

Determination of Powder X-ray Diffraction Patterns

X-ray diffraction data (e.g., FIGS. 1, 4, 6 and 8) were collected using a Philips X'Pert PW-3040-MPD X-ray diffractometer (Philips, Bothell, Wash.) set at 40 kV and 40 mA. Data was collected as a continuous scan at 0.02°/sec. between 40° to 40°.

Example 3

Determination of IR Spectra

IR data (e.g., FIGS. 2, 5, 7 and 9) were collected using a Digilab Excalibur FTS-4000 with Durasampl IR II ATR (Digilab, Randolph, Mass.) operated at 4 cm$^{-1}$ resolution and 16 scans between 500-4000 cm$^{-1}$. All samples were run in attenuated total reflection (ATR) mode.

Example 4

Determination of Raman Spectra

Raman spectral data (e.g., FIG. 3) were collected using PhAT Systems Optical Spectrophotometer (Kaiser Optical Systems, Inc., (Ann Arbor, Mich.) including a 785 nm Invictus NIR diode laser, a Raman RXN f/1.8 holographic imaging spectrograph with a 1024 CCD detector, and a PhAT probe. The sample was centered in the laser beam for measurement and scanned with an exposure time of 1 minute. Data was collected at 100-1800 cm$^{-1}$ with a wavenumber resolution of 3.8 cm$^{-1}$.

Example 5

DSC Measurement

DSC data (e.g., FIG. 10) were collected using a TA Instruments DSC 2920 Differential Scanning Calorimeter (TA Instruments, New Castle, Del.). Measurements were carried out in both closed pan and open pan modes on about 5-35 mg samples. The heating profile was from 25° C. to 170° C. at 5° C./min, or 25° C. to 120° C. at 5° C./min with a ten minute holding time at 120° C., or 25° C. to 135° C. at 5° C./min with a five minute holding time at 135° C., or 25° C. to 150° C. at 5° C./min with a one minute holding time at 150° C.

Example 6

Formation of Polymorph Forms C and D

A micronized sample of apratastat polymorph form A was subjected to three separate DSC experiments performed in the open pan mode as described in Example 5 above using the 120° C., 135° C., and 150° C. heating profiles. Each sample was cooled to ambient temperature and then recovered for powder X-ray diffraction (XRD) analysis as described in Example 2. A summary of the XRD results are shown in Table 5 below.

TABLE 5

| 120° C. | 135° C. | 150° C. |
|---|---|---|
| Form C | Form C | Amorphous |

A milled sample of apratastat polymorph form A was subjected to similar DSC conditions. A summary of the XRD results are shown in Table 6 below.

TABLE 6

| 120° C. | 135° C. | 150° C. |
|---|---|---|
| Form C + D | Form C + D | Form D |

Example 7

Evaporative Crystallization Method 1.5 g of apratastat was dissolved in 20 mL isopropanol with stirring at 30° C. The solution was distilled at 30° C. and 150 mm Hg vacuum to remove 12 mL isopropanol. The resulting solution was subjected to slow evaporation at 23° C. without stirring over 2 days to obtain a thick slurry. The slurry was filtered and the solid dried at 50° C. under vacuum to obtain 1.38 g of product.

Figure 11:
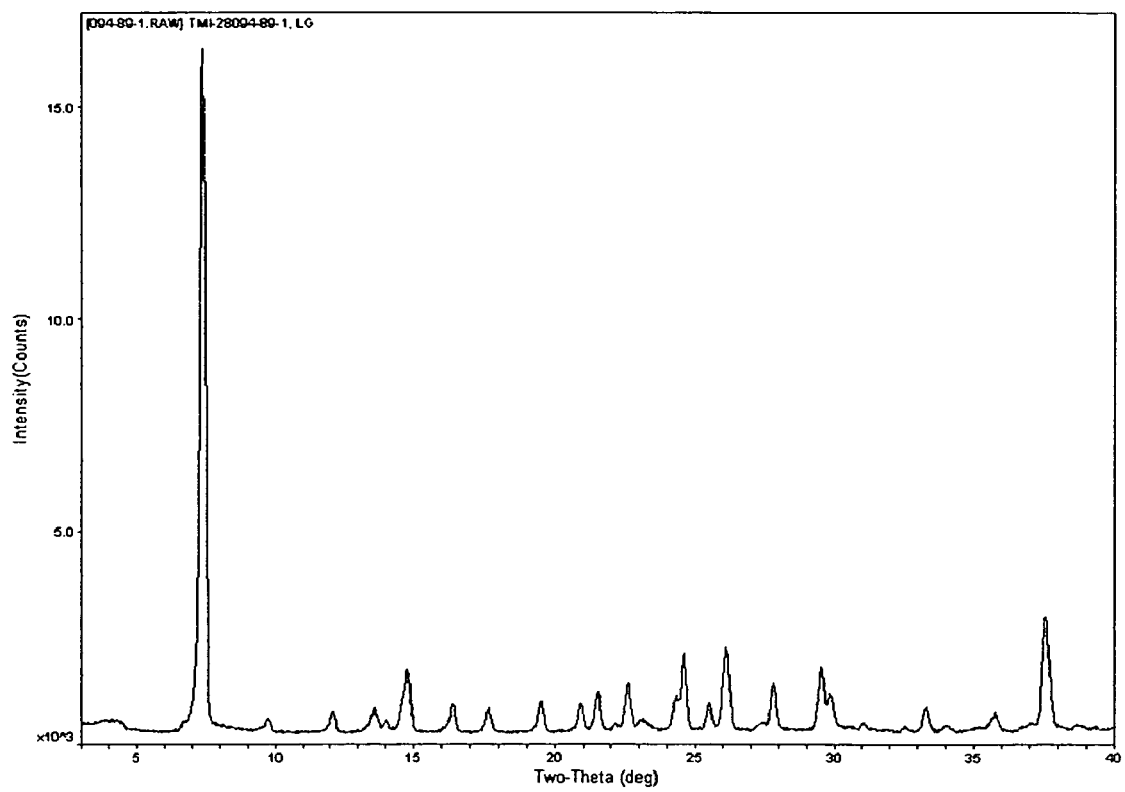
FIG. 11 depicts a powder X-ray diffration pattern of an apratastat sample prepared by the evaporative crystallization method described in Example 7.

Powder XRD data was collected using a Rigaku Miniflex Diffraction System (Rigaku MSC Inc., The Woodlands, Tex.) equipped with a Ni Kβ filter. The powder samples were deposited on a zero-background polished silicon sample holder. A normal focus copper x-ray tube was operated at 30 kV and 15 mA, and sample scanning was at 0.02 degree/step from 3.00° to 40.00° at 2θ. XRD data consistent with the product is provided in FIG. 11 and in Table 7 below.

TABLE 7

| Degree (2θ) | Intensity |
|---|---|
| 7.4 | 16090 |
| 9.7 | 302 |
| 12.1 | 500 |
| 13.6 | 558 |
| 14.0 | 266 |
| 14.8 | 1436 |
| 16.4 | 680 |

TABLE 7-continued

| Degree (2θ) | Intensity |
|---|---|
| 17.7 | 588 |
| 19.5 | 740 |
| 21.0 | 644 |
| 21.6 | 894 |
| 22.6 | 1099 |
| 23.2 | 260 |
| 24.3 | 741 |
| 24.6 | 1793 |
| 25.6 | 621 |
| 26.1 | 1943 |
| 27.5 | 184 |
| 27.9 | 1117 |
| 29.6 | 1458 |
| 29.9 | 780 |
| 33.3 | 585 |
| 35.8 | 454 |
| 37.6 | 2684 |

The XRD data for this form differ from that of polymorph form A at least by the presence of the peak at 37.6° and the relative attenuation of the peak at 27.5°.

Figure 12:
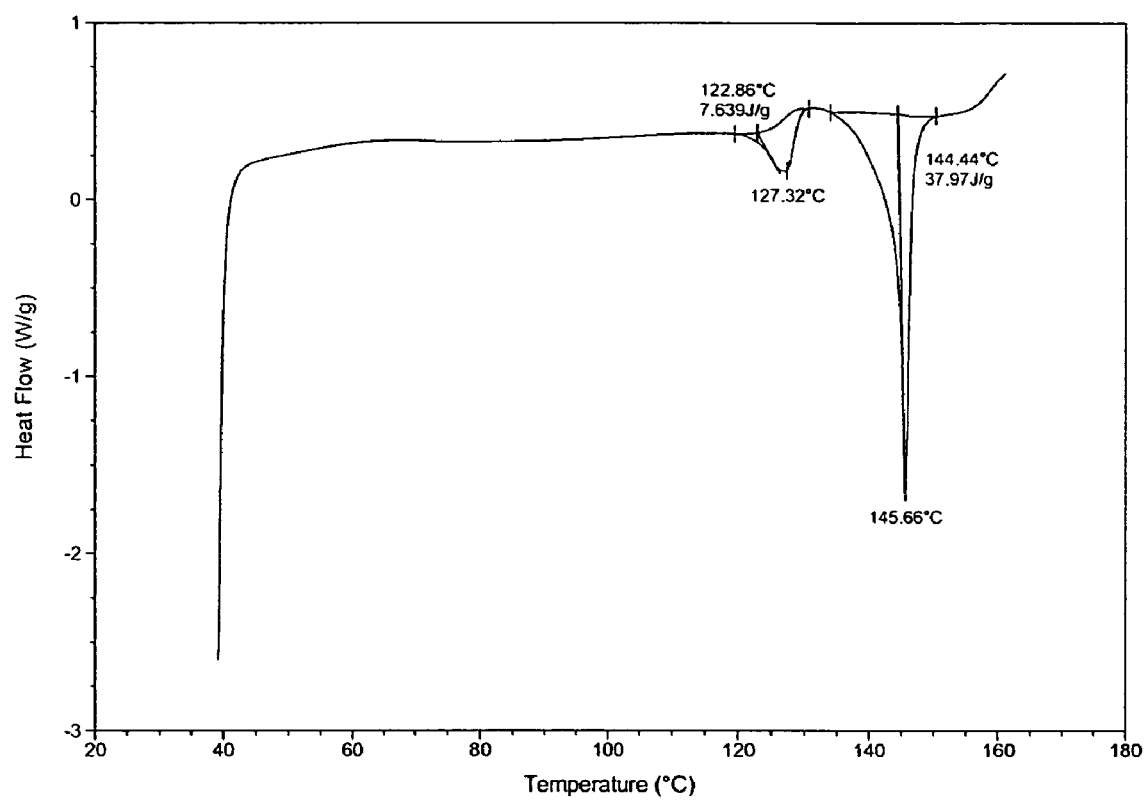
FIG. 12 depicts a differential scanning calorimetry profile of the sample from FIG. 11.

DSC data was collected for the product using a Q1000 DSC (TA Instruments, New Castle, Del.). About 1-5 mg of sample was used in a hermetically sealed aluminum pan (no pinhole). The sample was heated from 40° C.-200° C. at a ramp rate of 10° C./min. The DSC profile (FIG. 12) indicates two endotherms, one at about 127° C. and another at about 145° C.

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A crystalline polymorph (form A) of (3S)-N-hydroxy-4-({4-[(4-hydroxy-2-butynyl)oxy]phenyl}sulfonyl)-2,2-dimethyl-3-thiomorpholine carboxamide having a powder X-ray diffraction pattern comprising peaks at diffraction angle 2θ of about 7.5°, 19.6°, 24.7° and 26.2°.

2. The polymorph of claim 1, wherein the X-ray powder diffraction pattern further comprises peaks at diffraction angle 2θ of about 14.7°, 16.5°, 21.6°, 22.7°, 25.6° and 29.7°.

3. The polymorph of claim 1 having a powder X-ray diffraction pattern substantially as shown in FIG. 1.

4. The polymorph of claim 1 having an attenuated total reflection infrared spectrum substantially as shown in FIG. 2.

5. A pharmaceutical composition comprising the polymorph of claim 1 and at least one pharmaceutically acceptable carrier.

6. A method of preparing the polymorph of claim 1, comprising combining (3S)-N-hydroxy-4-({4-[(4-hydroxy-2-butynyl)oxy]phenyl}sulfonyl)-2,2-dimethyl-3-thiomorpholine carboxamide with a solvent comprising an alcohol to form a mixture, wherein the mixture is maintained at a temperature between about 30° C. and about 80° C. for a time and under conditions suitable for forming the polymorph.

7. The method of claim 6, wherein the alcohol is selected from the group consisting of methanol, ethanol, n-propanol, and isopropanol.

8. The method of claim 7, wherein the alcohol is isopropanol.

9. The method of claim 6, wherein the solvent further comprises water.

10. The method of claim 6, wherein the mixture is maintained at a temperature between about 50° C. and about 60° C.

11. The method of claim 6, further comprising the steps of adding water to the mixture to form a precipitate and collecting the precipitate.

12. A method of treating or inhibiting a disease or disorder mediated by TNF-α in a mammal, said method comprising providing to the mammal a therapeutically effective amount of a polymorph of claim 1, wherein the disease or disorder is rheumatoid arthritis, graft rejection, cachexia, fever, insulin resistance, septic shock, congestive heart failure, inflammatory disease of the central nervous system, inflammatory bowel disease or HIV infection.

13. A method of alleviating a symptom of a disease or disorder mediated by TNF-α in a mammal, said method comprising providing to the mammal a therapeutically effective amount of a polymorph of claim 1, wherein the disease or disorder is rheumatoid arthritis, graft rejection, cachexia, fever, insulin resistance, septic shock, congestive heart failure, inflammatory disease of the central nervous system, inflammatory bowel disease or HIV infection.

14. The polymorph of claim 2, wherein the X-ray powder diffraction pattern further comprises peaks at diffraction angle 2θ of about 9.8°, 13.7°, 17.8°, 21.0°, 23.3°, 24.5°, 27.5°, and 28.0°.

15. The polymorph of claim 1, wherein the X-ray powder diffraction pattern comprises peaks at diffraction angle 2θ of about 6.8°, 7.5°, 9.8°, 12.2°, 13.7°, 14.1°, 14.7°, 14.9°, 15.3°, 16.5°, 17.8°, 18.9°, 19.6°, 20.1°, 21.0°, 21.6°, 22.2°, 22.7°, 23.3°, 23.4°, 24.5°, 24.7°, 25.6°, 26.2°, 27.5°, 28.0°, 28.6°, 29.0°, 29.7°, 30.3°, 30.6°, 31.1°, 31.5°, 32.0°, 32.7°, 33.5°, 34.2°, 35.0°, 35.8°, 36.8°, 37.2°, 37.8°, 38.2°, 38.9°, 39.1°, 39.4°, and 39.9°.

16. The polymorph of claim 1 having an attenuated total reflection infrared spectrum comprising bands at about 3380 $cm^{-1}$, 3220 $cm^{-1}$, 2970 $cm^{-1}$, 2930 $cm^{-1}$, 1680 $cm^{-1}$, 1650 $cm^{-1}$, 1590 $cm^{-1}$, 1580 $cm^{-1}$, 1500 $cm^{-1}$, 1450 $cm^{-1}$, 1370 $cm^{-1}$, 1330 $cm^{-1}$, 1300 $cm^{-1}$, 1250 $cm^{-1}$, 1150 $cm^{-1}$, 1090 $cm^{-1}$, and 1050 $cm^{-1}$.

17. A crystalline polymorph (form B) of (3S)-N-hydroxy-4-({4-[(4-hydroxy-2-butynyl)oxy]phenyl}sulfonyl)-2,2-dimethyl-3-thiomorpholine carboxamide having a powder X-ray diffraction pattern comprising peaks at diffraction angle 2θ of about 7.6°, 19.5°, 22.9°, and 26.4°.

18. The polymorph of claim 17, wherein the X-ray powder diffraction pattern further comprises peaks at diffraction angle 2θ of about 10.4°, 11.1°, and 11.3°.

19. The polymorph of claim 18, wherein the X-ray powder diffraction pattern further comprises peaks at diffraction angle 2θ of about 13.7°, 14.1°, 14.7°, 16.6°, 21.8°, and 29.8°.

20. The polymorph of claim 17, wherein the X-ray powder diffraction pattern comprises peaks at diffraction angle 2θ of about 7.6°, 9.8°, 10.4°, 11.1°, 11.3°, 12.2°, 13.5°, 13.7°, 14.1°, 14.7°, 15.1°, 15.6°, 16.6°, 17.9°, 19.0°, 19.5°, 20.3°, 20.8°, 21.2°, 21.8°, 22.2°, 22.9°, 23.3°, 24.6°, 24.8°, 25.7°, 26.4°, 27.0°, 27.5°, 28.2°, 29.0°, 29.2°, 29.8°, 30.4°, 30.8°, 31.3°, 31.6°, 33.0°, 33.4°, 33.8°, 34.3°, 35.1°, 36.0°, 36.9°, 37.6°, 38.3°, 39.0°, 39.2°, and 39.6°.

21. The polymorph of claim 17 having a powder X-ray diffraction pattern substantially as shown in FIG. 4.

22. A crystalline polymorph (form C) of (3S)-N-hydroxy-4-({4-[(4-hydroxy-2-butynyl)oxy]phenyl}sulfonyl)-2,2-dimethyl-3-thiomorpholine carboxamide having a powder X-ray diffraction pattern comprising peaks of 2θ of about 7.5°, 13.4°, 15.5°, 17.8°, and 21.8°.

23. The polymorph of claim 22, wherein the X-ray powder diffraction pattern comprises peaks at diffraction angle 2θ of about 6.1°, 7.5°, 8.9°, 9.9°, 10.4°, 10.9°, 11.3°, 12.1°, 13.1°, 13.4°, 13.6°, 14.1°, 14.7°, 15.1°, 15.5°, 16.3°, 16.5°, 17.0°, 17.8°, 16.4°, 19.1°, 19.5°, 19.8°, 20.3°, 20.5°, 21.0°, 21.8°, 22.2°, 22.9°, 23.3°, 24.4°, 24.7°, 25.4°, 25.8°, 26.2°, 26.5°, 27.0°, 27.4°, 27.9°, 28.4°, 29.3°, 30.0°, 30.5°, 30.7°, 31.3°, 32.0°, 32.3°, 33.1°, 33.4°, 33.7°, 34.6°, 35.2°, 35.9°, 36.4°, 37.0°, 37.7°, 38.2°, 38.8°, 39.2°, 39.5°, and 39.9°.

24. The polymorph of claim 22 having a powder X-ray diffraction pattern substantially as shown in FIG. 6.

25. A crystalline polymorph (form d) of (3S)-N-hydroxy-4-({4-[(4-hydroxy-2-butynyl)oxy]phenyl}sulfonyl)-2,2-dimethyl-3-thiomorpholine carboxamide having a powder X-ray diffraction pattern comprising peaks of 2θ of about 8.3°, 18.5°, 19.0°, 20.6°, 24.9°, and 28.5°.

26. The polymorph of claim 25, wherein the X-ray powder diffraction pattern comprises peaks at diffraction angle 2θ of about 8.3°, 9.2°, 9.5°, 10.1°, 10.7°, 11.1°, 12.4°, 12.6°, 12.8°, 13.5°, 13.6°, 13.9°, 14.1°, 14.5°, 14.8°, 15.1°, 15.5°, 15.8°, 16.1°, 16.4°, 16.6°, 17.0°, 17.2°, 17.8°, 18.5°, 19.0°, 19.5°, 19.8°, 20.3°, 20.6°, 21.2°, 21.6°, 21.8°, 22.3°, 22.8°, 23.6°, 24.4°, 24.9°, 25.4°, 25.8°, 26.2°, 26.7°, 27.0°, 27.6°, 28.0°, 28.5°, 28.8°, 29.1°, 29.6°, 30.0°, 30.7°, 31.4°, 32.0°, 32.3°, 32.9°, 33.7°, 34.0°, 34.4°, 34.9°, 35.8°, 36.4°, 36.7°, 37.6°, 38.0°, 38.3°, 38.6°, 39.0°, and 39.3°.

Figure 8:
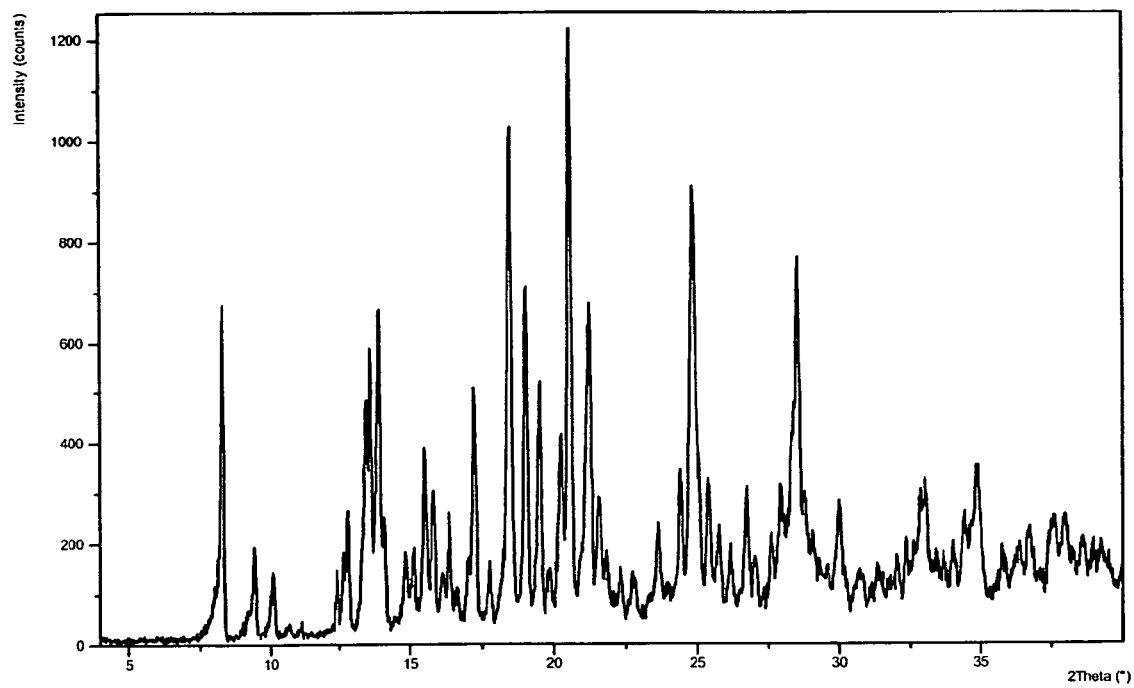
FIG. 8 depicts a powder X-ray diffration pattern of apratastat polymorph form D.

27. The polymorph of claim 25 having a powder X-ray diffraction pattern substantially as shown in FIG. 8.

* * * * *